(12) United States Patent
Wochele

(10) Patent No.: US 8,770,448 B2
(45) Date of Patent: Jul. 8, 2014

(54) DROP DISPENSER

(71) Applicant: Matthias Wochele, Rielasingen (DE)

(72) Inventor: Matthias Wochele, Rielasingen (DE)

(73) Assignee: Aptar Radolfzell GmbH, Radolfzell (DE)

( * ) Notice: Subject to any disclaimer, the term of this patent is extended or adjusted under 35 U.S.C. 154(b) by 0 days.

(21) Appl. No.: 13/622,665

(22) Filed: Sep. 19, 2012

(65) Prior Publication Data

US 2013/0075431 A1    Mar. 28, 2013

(30) Foreign Application Priority Data

Sep. 23, 2011  (DE) .......................... 10 2011 083 355

(51) Int. Cl.
*B65D 47/18* (2006.01)
*B01L 3/00* (2006.01)
*B01L 3/02* (2006.01)

(52) U.S. Cl.
CPC . *B65D 47/18* (2013.01); *B01L 3/00* (2013.01); *B01L 3/0272* (2013.01)
USPC .......................................... 222/420; 604/295

(58) Field of Classification Search
CPC .......... B65D 47/18; B01L 3/00; B01L 3/0271
USPC ............................. 222/420–422; 604/295, 300
See application file for complete search history.

(56) References Cited

U.S. PATENT DOCUMENTS

| | | | | |
|---|---|---|---|---|
| 5,221,017 A | * | 6/1993 | Cistone et al. | 215/235 |
| 5,373,964 A | * | 12/1994 | Moore | 222/1 |
| 6,869,421 B2 | * | 3/2005 | Hanley | 604/295 |
| 7,008,979 B2 | * | 3/2006 | Schottman et al. | 523/334 |
| 7,281,876 B2 | * | 10/2007 | Kwon | 401/265 |
| 7,950,391 B2 | * | 5/2011 | Fuchs | 128/205.13 |
| 8,007,480 B2 | * | 8/2011 | Kawashiro et al. | 604/289 |
| 8,247,039 B2 | | 8/2012 | Mozetic et al. | |
| 2004/0079766 A1 | * | 4/2004 | Kokubo | 222/212 |
| 2010/0216943 A1 | | 8/2010 | Cavaleiro et al. | |

FOREIGN PATENT DOCUMENTS

| | | |
|---|---|---|
| DE | 11 2006 001 297 T5 | 4/2008 |
| DE | 10 2007 049 587 A1 | 4/2009 |
| EP | 0 401 022 A1 | 12/1990 |
| EP | 0 431 885 A1 | 6/1991 |
| FR | 2 655 623 A1 | 6/1991 |
| WO | WO 84/00707 | 3/1984 |
| WO | WO 2008/068775 A2 | 6/2008 |

OTHER PUBLICATIONS

Examination Report of German Patent Office issued in German Application No. 10 2011 083 355.2 dated Mar. 12, 2012 (5 pages).
European Patent Office Search Report issued in Europe Application No. 12 18 3511.0 dated Dec. 20, 2012 with English translation of category of cited documents (7 pages).

* cited by examiner

*Primary Examiner* — Lien Ngo
(74) *Attorney, Agent, or Firm* — Flynn, Thiel, Boutell & Tanis, P.C.

(57) ABSTRACT

Drop dispenser for releasing a pharmaceutical liquid in drop form, with a housing, a liquid storage and a discharge opening, which penetrates a wall of the housing and to which an outlet valve is assigned, for extracting the liquid. The discharge opening is surrounded by a drop-formation area on the outside of the housing, wherein this drop-formation area, at least in an outer region with respect to an alignment of the drop dispenser with the discharge opening pointing vertically downwards, has a shape tapering downwards and towards the discharge opening. The drop dispenser allows the release of drops with a constant size and shortens drying time.

8 Claims, 2 Drawing Sheets

DROP DISPENSER

CROSS REFERENCE TO RELATED APPLICATION

This application claims priority from German Application No. 10 2011 083 355.2, filed Sep. 23, 2011, the disclosure of which is hereby incorporated by reference in its entirety into this application.

FIELD OF THE INVENTION

The invention relates to a drop dispenser for releasing a pharmaceutical liquid in drop form. In this case, such a generic drop dispenser has a housing and a liquid storage, as well as a discharge opening, which penetrates a wall of the housing and to which an outlet valve is assigned, for extracting the liquid.

BACKGROUND OF THE INVENTION

Drop dispensers are generally known from the prior art for administering various medicaments. They have a liquid storage, which can for example be embodied as a squeeze bottle and brings about delivery of the liquid through the discharge opening as a result of compression and simultaneously having the discharge opening pointing downwards. If used as intended, a drop is formed on the outside of the discharge opening in such a drop dispenser, with said drop separating from the dispenser once it has reached a sufficient size that leads to the greatest part of the discharged amount of liquid pinching off in the form of a main drop. A drop remainder, which can hardly be avoided by technical means, usually remains in the surroundings of the discharge opening.

Since the dose of medicaments which are extracted in drop form is usually specified in terms of the number of drops, obtaining a constant size of the separating main drop is of great importance.

The aforementioned drop remainder was found to be problematic in the past. In the case of drop dispensers that do not have an outlet valve assigned to the discharge opening, this drop remainder is usually suctioned back into the bottle by the negative pressure previously formed in the liquid storage. However, in the case of generic drop dispensers that usually have an outlet valve which opens depending on the pressure, the return path back into the drop dispenser is closed off for the drop remainder after the end of the discharge process, and so the drop remainder remains on the outside of the discharge opening. This is problematic because this drop remainder can become a carrier of a contamination. It is therefore desirable that the drop remainder evaporates as quickly as possible.

SUMMARY OF THE INVENTION

It is an object of the invention to develop a generic drop dispenser to the extent that it enables particularly quick evaporation of the drop remainder. It is furthermore an object to provide a drop dispenser in which the liquid volume of each drop is largely constant.

According to the invention, this object as per a first aspect of the invention is achieved by virtue of the fact that the discharge opening is surrounded by a drop-formation area on the outside of the housing, wherein this drop-formation area, at least in an outer region with respect to an alignment of the drop dispenser with discharge opening pointing vertically downwards, has a shape tapering downwards and towards the discharge opening and moreover has a hydrophilic design.

Hence, the invention in particular relates to the shaping and design of the drop-formation area, which is that area on which, when used as intended, the drop to be released adheres before it, at least to the greatest part, separates from the dispenser. The downwards tapering shaping of the outer region of this drop-formation area should in particular be understood to mean a cone-like or frustum-like shaping, with e.g. ball-like shapes also being possible. The lateral area thereof is arranged on the outside of the discharge opening and has a hydrophilic embodiment.

A hydrophilic embodiment of this aforementioned area is understood to mean that, under reference conditions of water at 20° C., a contact angle specifying the degree of hydrophilicity between the aforementioned water and the area is 20° or less, more particularly 10° or less.

The drop-formation area surrounding the discharge opening having a combination of a taper and a hydrophilic design has proven to be advantageous, particularly in respect of the evaporation time of the drop remainder. Compared to a planar design of a drop-formation area and under the assumption of an equal external diameter of the drop remainder remaining on the dispenser, this design provides a larger area over which the drop remainder is distributed. Moreover, it was observed that the drop remainder usually has a smaller volume.

This enlarged area, on which the volumetrically reduced drop remainder is distributed, leads to a reduction in the drying time. Thus, it was possible to observe under otherwise unchanging conditions that a water drop on a planar drop-formation area has an approximate 4-fold evaporation time compared to a drop-formation area with the same external diameter and a design which according to the invention, at least in sections, has a conical/tapering and hydrophilic.

In principle, this advantage of the reduced evaporation time is also provided if it is not only a delimited drop-formation area which has a hydrophilic design, but rather the whole dispenser on its outside. However, in order to create a defined drop size it is considered to be advantageous if the drop-formation area is spatially delimited. By way of example, this can be achieved by virtue of the drop-formation area being surrounded by a surrounding area which has a lower hydrophilicity than the drop-formation area. The hydrophilicity of the surrounding area surrounding the drop-formation area is preferably such that, under the aforementioned boundary conditions, it leads to a contact angle greater than 20°, preferably greater than 45°. The jump thus provided in respect of the hydrophilicity between the drop-formation area and the surrounding area causes the separation of the main drop from the drop remainder usually to take place without liquid reaching the region of the surrounding area in advance via the outer limit of the drop-formation area.

Alternatively, or in addition thereto, it is possible to delimit the drop-formation area on the outside by a boundary edge which has a radius of curvature of at most 0.2 mm. Such a boundary edge likewise leads to an increase in the tendency of the main drop to detach from the drop remainder before liquid leaves the hydrophilic drop-formation area via the aforementioned boundary edge. The boundary edge is preferably implemented together with the surrounding area of lesser hydrophilicity. However, an embodiment is also by all means feasible, in which the area outside of the boundary edge likewise has a hydrophilic design and the boundary edge therefore has the sole responsibility for the liquid not passing over the boundaries of the drop-formation area during the drop formation.

The drop-formation area has such dimensions that a parallel projection of the drop-formation area in a horizontal plane—with respect to an alignment of the drop dispenser with a discharge opening pointing vertically downwards—has a projection area of between 0.4 mm² and 24 mm², preferably a projection area of between 3 mm² and 7 mm².

Here, the projection area formed by the parallel projection on a horizontal plane should be understood to mean the projection area determined only by the outer edges of the drop-formation area. The projection of the discharge opening is therefore likewise part of this projection area. The aforementioned size interval between 0.4 mm² and 24 mm² was found to be suitable for the formation of drops between 10 µl and 80 µl. The drop size of approximately 30 to 40 µl, which is often desired, is achieved by the smaller of the aforementioned intervals.

As a result of the tapering or conical shaping, the drop-formation area and the outer areas in the region of the discharge opening naturally add up to an overall area which is greater than the aforementioned values because the latter relate to the projection. It is precisely this actual drop-formation area which is enlarged compared to the projection area that ensures the reduced evaporation time.

There are a number of options in respect of producing the desired hydrophilicity at the drop-formation area. Thus, in a first preferred variant, provision is made for partial coating of a plastic forming the wall of the housing to be used for establishing the hydrophilicity. To the extent that provision is made for a surrounding area with a lower hydrophilicity around the drop-formation area, the former can be formed by an uncoated section of this plastic. The hydrophilicity can also be obtained by partial irradiation. Thus, in this embodiment, there is a coating/irradiation of a previously non-hydrophilic plastic in order to generate the hydrophilicity. The basic properties of the plastic can be used in the region of the surrounding area for the purpose of the weaker hydrophilicity provided there.

As an alternative to this embodiment, it is possible for the hydrophilicity of the drop-formation area to be established by a housing section which, as a whole, consists of a hydrophilic material. To the extent that a surrounding area with low hydrophilicity is desired in this case, it can more particularly be established by virtue of the surface of a second housing section, which is fixedly connected to the first housing section, forming this surrounding area. In particular, the first housing section can be inserted in a cut-out of the second housing section. Thus, it is possible to dispense with coating processes or irradiation processes of individual housing sections in this variant. Rather, use is made of housing sections made of materials with differing hydrophilicity.

By way of example, in order to make the surfaces hydrophilic, these can be coated with a polymer with hydrophilic properties. Examples of polymers with hydrophilic properties are 2-hydroxyethyl methacrylate (HEMA), glyceryl methacrylate (GMA), glyceryl methyl methacrylate (GMMA), N-vinylpyrrolidone (NVP), methacrylic acid (MAA), methyl methacrylate (MMA), polyurethane (PU), polyvinyl alcohol (PVA) or polydextrose. These materials are not only suitable as coating materials. Rather, the corresponding component can also consist thereof in its entirety. Vapour deposition of a metal such as aluminum generally also brings about a significant increase in the hydrophilicity.

The surface region in question can also be made to be hydrophilic by plasma treatment, for example. This is generally carried out in a plasma reactor at very low pressure. The plasma contains reactive species such as e.g. ions and free radicals, which react with the surface and can modify it chemically, always depending on the nature of the physical properties of the plasma. Oxygen or argon plasma is often used for hydrophilizations.

Additionally, reference is also made to DE 112006001297 T5 and DE 102007049587 A1 in respect of establishing the desired hydrophilicity, the disclosure of which in respect of the production of hydrophilic materials and surfaces is made to be the subject matter of the present disclosure by reference.

The use of nano-crosslinked silicon-organic compounds was found to be particularly advantageous.

According to a second aspect of the invention, which is preferably implemented together with the already mentioned first aspect of the invention, provision is made for the drop-formation area in a generic drop dispenser to be formed by an external surface of a drop-formation body of the housing, with this drop-formation body having the shape of a spherical cap, the sphere surface of which is greater than the sphere surface of a hemisphere with the same diameter.

In the case of such an embodiment, provision is therefore made for a drop-formation body which appears like a section of a sphere which exceeds a hemisphere. The necessarily given deviation from the spherical shape in the region of the outlet opening can be ignored in this case. All that is important in respect of this aspect of the invention is that the drop-formation area forms an equatorial region of the sphere-like body and exceeds the latter towards both sides. The drop-formation body is preferably connected to other sections of the housing by a web that is reduced compared to the diameter of the sphere. The embodiment of the drop-formation body as a body which in terms of size exceeds a hemisphere renders it possible to obtain constant drop sizes independently of a precise vertical alignment of the drop dispenser. This at least affords the possibility of an angle of the drop dispenser of up to 15° from the vertical alignment having no effect on the size of the drop.

BRIEF DESCRIPTION OF THE DRAWINGS

Apart from the claims, further aspects and advantages of the invention also emerge from the following description of preferred exemplary embodiments of the invention, which are explained on the basis of the figures, wherein:

DETAILED DESCRIPTION

Figure 1:
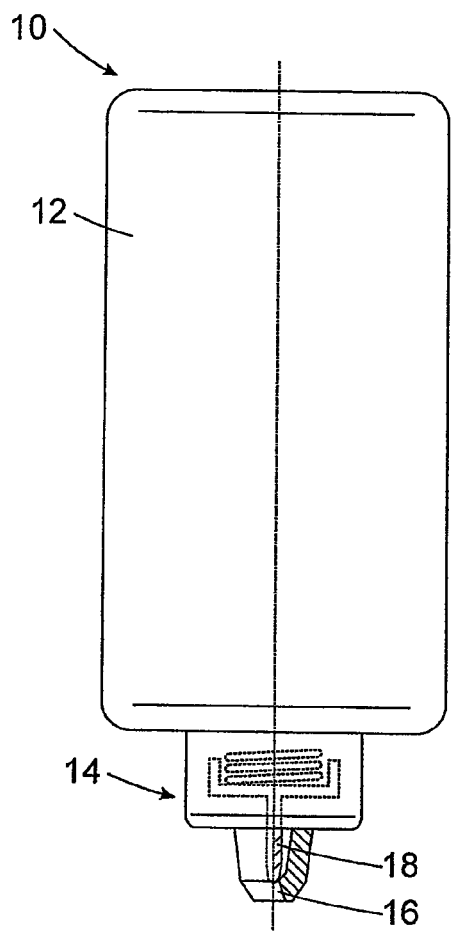
FIG. 1 shows a drop dispenser according to the invention in an overall view.

FIG. 1 shows an overall view of a drop dispenser according to the invention. The drop dispenser 10 has a liquid storage 12, which is embodied as a squeeze bottle. In a usage position, an outlet unit 14 of the drop dispenser 10 is directed downwards. This outlet unit comprises an outlet opening 16, which is closed by a valve pin 18 in the closed state of the dispenser 10. The valve pin 18 is part of a valve, indicated by dashed lines in FIG. 1, which opens and closes depending on the liquid pressure within the drop dispenser 10. In order to discharge liquid from the liquid storage 12 through the outlet opening 16, the liquid storage 12 is compressed by hand. This causes an increase in pressure and opens the valve by displacing the valve pin 18. If used as intended, the emerging liquid collects in the region of the outlet opening 16 and forms a drop there, the greater part of which separates from the dispenser after a specific size is reached while a smaller part, referred to as drop remainder, remains in the region of the outer area of the outlet unit 14.

Figure 2A:
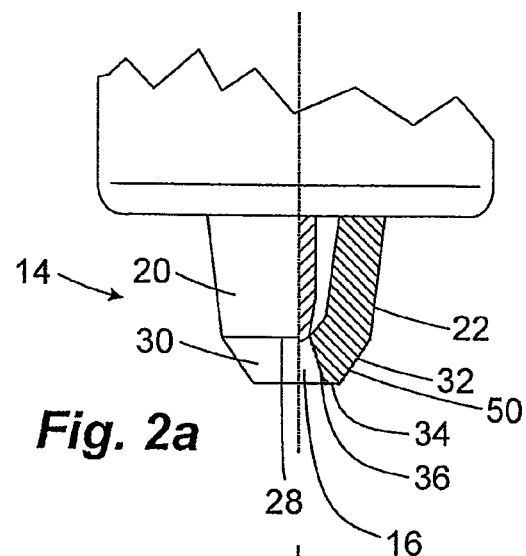
FIGS. 2a-2c show a first embodiment of the outlet unit of the drop dispenser in FIG. 1.
Figure 2B:
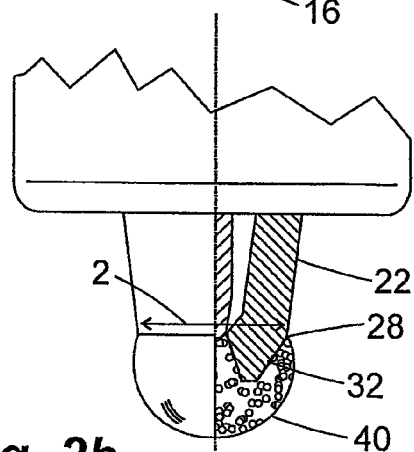
Figure 2C:
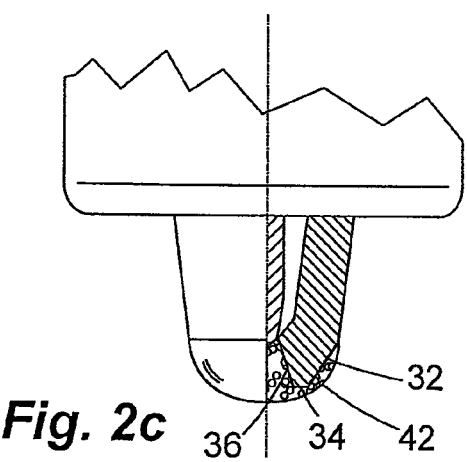

FIGS. 2a to 2c show the outlet unit 14 of the dispenser in FIG. 1 in magnified form. The constructive design of the discharging arrangement 14 is explained in more detail with reference to FIG. 2a. It is possible to identify that the outer shape of the outlet unit 14 has two mutually adjacent frustum-shaped sections 20, 30. If used as intended, the lateral area 32 of the conical section 30 serves for the adhesion of a drop to be released before the latter separates from the drop dispenser 10. The end area 34 and the inner surface 36, which surround the outlet opening 16 likewise serve for the adhesion of this drop. In order to simplify this adhesion and in particular to cause the liquid emerging at the outlet opening 16 to wander upwards along the lateral area 32 against gravity, the aforementioned areas 32, 34, 36 have a hydrophilic design. In FIGS. 2a, 2b and 2c, this is made clearer by the dashed line drawn here. In this region of the dashed line, the surface of the integral body, which forms both the cone section 30 and the cone section 20, has a hydrophilic design as a result of a coating 50 or, alternatively, as a result of irradiation. By contrast, the lateral area 22 of the upper frustum-shaped section 20 adjoining the lateral area 32 does not have a hydrophilic design but rather has an unchanged material surface.

The material of the component forming the frustum sections 20, 30 can be HDPE, for example. As a material, the latter is not hydrophilic, and so a contact angle with water as a liquid is approximately 80°. In the region of the hydrophilic surfaces 32, 34, 36, this contact angle is less than 5° as a result of the coating.

A sharp-edged boundary edge 28 is provided between the lateral areas 22, 32, said edge having a radius of curvature of approximately 0.2 mm. This boundary edge supports the functionality explained below when discharging a drop.

FIG. 2b shows the process of drop creation. As a result of applying a force on the liquid storage 12, the liquid is, in the case of a slightly opened outlet valve, pressed through the discharge opening 16 and collects as sketched out in FIG. 2b. Here, the fact that the liquid creeps upwards along the outside of the lateral area 32 but does not pass beyond the boundary edge 28 as a result of the geometric design thereof and as a result of the hydrophobic design of the lateral area 22 should be highlighted in particular. Hence the external diameter 2 of the drop-formation area is clearly defined.

As the volume of the drop 40 increases so does its tendency to separate from the drop dispenser 10. When a size of the drop, which is dependent on, in particular, the drop-formation area geometry, is reached, the latter is pinched off (not illustrated) and so the greater part of the drop, the main drop, separates from the dispenser 10. All that still remains on the dispenser 10 is the drop remainder 42, which is illustrated in FIG. 2c. Until now it has not been possible to completely avoid a drop remainder remaining. However, as shown in FIG. 2c, the described and illustrated design can bring about a very advantageous shape of this drop remainder 42. As a result of the relatively large drop-formation area 32, 34, 36, which is significantly larger than a planar circular area with the diameter 2, the remaining amount of liquid is distributed rather well, and so the layer thickness of the liquid is small. The drop remainder 42 as per FIG. 2c will therefore evaporate quickly. In addition to the comparatively large drop-formation area 32, 34, 36, what is also responsible for this is that, as it were, a substantial part of the internal volume of the drop remainder 42 is filled by the cone section 30.

Figure 3:
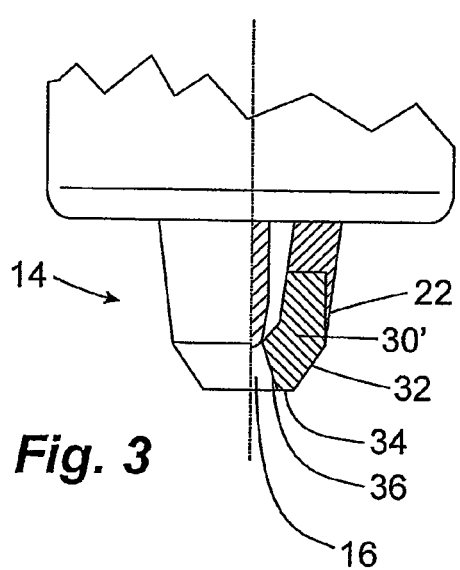
FIG. 3 shows a second alternative embodiment of the outlet unit of the drop dispenser.

FIG. 3 shows an alternative embodiment which corresponds to the previous embodiment in terms of its functionality. The distinctive feature of the embodiment according to FIG. 3 lies in the fact that the lateral area 32, the end area 34 and the area 36 pointing towards the outlet opening 16 are provided on a separate body 30', which consists of an inherently hydrophilic material. By way of example, this material can have been made to be hydrophilic by inserted additions. This separate body 30' is inserted into a cut-out of a body 20' forming the lateral area 22 and is held therein by a force fit, for example.

Figure 4A:
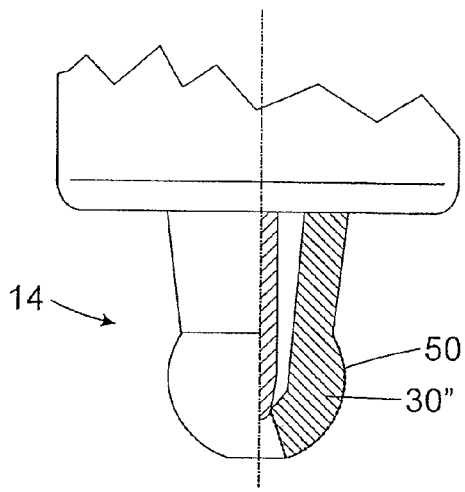
FIGS. 4a-4c show a third alternative embodiment of the outlet unit of the drop dispenser.

The embodiment of FIGS. 4a to 4c is once again similar to the embodiment in FIGS. 2a to 2c because here provision is also made for an integral body forming the outside of the discharge unit 14, which body is merely partly provided with a coating 50 that leads to hydrophilic properties. However, deviating from the embodiment in FIGS. 2a to 2c, the distinctive feature is implemented here that the outer area of the discharge unit 14 in sections has the shape of a spherical cap 30", the outside of which is provided with the coating 50 as specified above. The effect of this outer coating and the aforementioned shape is similar to the effect explained with reference to FIGS. 2a to 2c. The enlarged surface can once again achieve that a drop remainder which remains after the discharge can quickly evaporate.

Figure 4B:
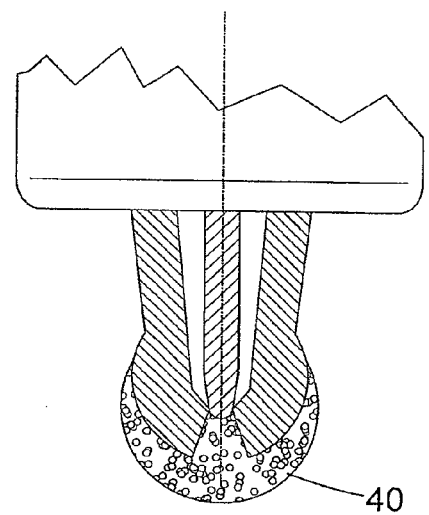
Figure 4C:
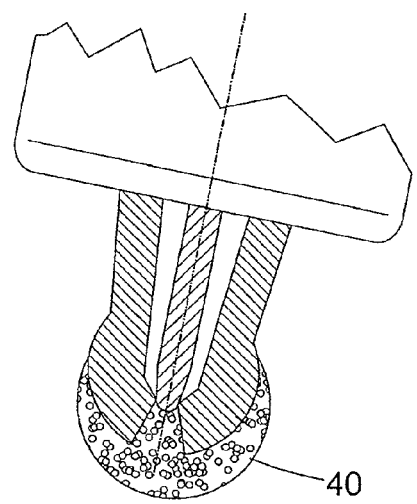

Here, the distinctive feature of the spherical cap-shaped surface emerges from FIGS. 4b and 4c in particular. It is possible to identify that the spherical cap shape leads to the volume of the forming drop 40 and the size of the drop 40 at the instant of separation from the drop dispenser 10 no longer depending on the precise alignment of the drop dispenser. Thus, FIG. 4c shows that even if the drop dispenser 10 is tilted by about 15°, the volume of the drop is not influenced. Hence a precise dose is ensured even if the drop dispenser 10 is not handled very precisely.

The invention claimed is:

1. A drop dispenser for releasing a pharmaceutical liquid in drop form, comprising:
    a housing;
    a liquid storage; and
    a discharge opening, which penetrates a wall of the housing and to which an outlet valve is assigned, for extracting the liquid;
    wherein the discharge opening is surrounded by a drop-formation area on an outside of the housing, wherein the drop-formation area, at least in an outer region with respect to an alignment of the drop dispenser with the discharge opening pointing vertically downwards, has a shape tapering downwards and towards the discharge opening and has a hydrophilic design; and
    wherein the drop-formation area is surrounded by a surrounding area which has a lower hydrophilicity than the drop-formation area.

2. The drop dispenser according to claim 1, wherein the drop-formation area is delimited on the outside by a boundary edge, with this boundary edge having a radius of curvature of at most about 0.2 mm.

3. The drop dispenser according to claim 1, wherein the drop-formation area has such dimensions that a parallel projection of the drop-formation area in a horizontal plane, with respect to an alignment of the drop dispenser with a discharge opening pointing vertically downwards, has a projection area of between about 0.4 mm$^2$ and about 24 mm$^2$.

4. The drop dispenser according to claim 1, wherein a hydrophilicity of the drop-formation area is established by partial coating of a plastic forming a wall of the housing, with the surrounding area being formed by an uncoated section of the plastic.

5. The drop-Drop dispenser according to claim 1, wherein a hydrophilicity of the drop-formation area is established by a housing section which, as a whole, consists of a hydrophilic material, with the surrounding area being formed by the surface of a second housing section, into which the first housing section is inserted.

6. The drop dispenser according to claim 1, wherein the drop-formation area is formed by an external surface of a drop-formation body of the housing, with the drop-formation body having a shape of a spherical cap, a cross-sectional area of the drop-formation body along a line parallel to a discharge direction of the pharmaceutical liquid forming more than 180° of a circle.

7. A drop dispenser for releasing a pharmaceutical liquid in drop form, comprising:
   a housing;
   a liquid storage; and
   a discharge opening, which penetrates a wall of the housing and to which an outlet valve is assigned, for extracting the liquid;
   wherein a drop-formation area is formed by an external surface of a drop-formation body of the housing, with the drop-formation body having the shape of a spherical cap, a cross-sectional area of the drop-formation body along a line parallel to a discharge direction of the pharmaceutical liquid forming more than 180° of a circle.

8. The drop dispenser according to claim 3, wherein the projection area is between about 3 mm$^2$ and about 7 mm$^2$.

* * * * *